(12) United States Patent
Baran-Harper et al.

(10) Patent No.: US 10,401,303 B1
(45) Date of Patent: Sep. 3, 2019

(54) LIGHTING APPARATUS FOR CONVEYORS (71) Applicant: P & P OPTICA INC., Waterloo (CA)

(72) Inventors: Alexander Baran-Harper, Waterloo (CA); Allan Hamzic, Kitchener (CA)

(73) Assignee: P & P OPTICA INC., Waterloo, Ontario (CA)

( * ) Notice: Subject to any disclaimer, the term of this patent is extended or adjusted under 35 U.S.C. 154(b) by 0 days.

(21) Appl. No.: 15/998,452

(22) Filed: Aug. 15, 2018

(51) Int. Cl.
*G01N 21/88* (2006.01)
*G01N 21/956* (2006.01)
*G01N 21/89* (2006.01)
*G01N 21/84* (2006.01)

(52) U.S. Cl.
CPC ..... *G01N 21/8806* (2013.01); *G01N 21/8901* (2013.01); *G01N 21/956* (2013.01); *G01N 2021/845* (2013.01); *G01N 2021/8841* (2013.01)

(58) Field of Classification Search
CPC . B26D 5/007; B26D 5/34; B26D 7/30; B26D 5/32; B26D 2210/02; B26D 5/00; B07C 5/342; B07C 5/3422; B07C 5/365; B07C 5/466; G01N 21/8806; G01N 21/8901; G01N 21/90; G01N 21/896; G01N 21/909; G01B 11/245; G01B 11/25; B65H 43/08; B65H 7/14; G09F 19/22; G06Q 20/208; B23Q 17/24; B25G 2201/0211; B27B 31/06; G01M 11/081
USPC ... 348/61, 86, 89, 91–92, 94, 125, 142, 180, 348/184
See application file for complete search history.

(56) References Cited

U.S. PATENT DOCUMENTS

| 4,476,981 | A | * | 10/1984 | Yoshida | B65G 47/82 198/370.07 |
| 4,805,778 | A | * | 2/1989 | Nambu | A01K 43/00 209/3.3 |
| 4,944,411 | A | * | 7/1990 | Fukushima | B07C 5/00 209/510 |
| 2008/0187637 | A1 | * | 8/2008 | Spiegel | A21C 9/04 426/383 |
| 2010/0121484 | A1 | * | 5/2010 | Blanc | B07C 5/3422 700/223 |
| 2013/0135101 | A1 | * | 5/2013 | Kotula | G08B 3/10 340/540 |
| 2014/0021260 | A1 | * | 1/2014 | Cherry | G06K 7/01 235/475 |
| 2017/0346996 | A1 | * | 11/2017 | Kida | G06T 7/74 |

* cited by examiner

*Primary Examiner* — Hung Q Dang
(74) *Attorney, Agent, or Firm* — Perry + Currier Inc.

(57) ABSTRACT

A lighting apparatus which indicates a condition and positions of a product moving along a conveyor is provided. The lighting apparatus includes one or more sensors configured to capture a condition reading of the product and a position reading of the product; a line of lights configured for installation proximate to the conveyor and along the path of the conveyor, the lights of the line of lights configurable between different visual states; a controller to determine a condition of the product based on the condition reading, determine an initial position of the product based on the position reading, generate a schedule for controlling visual states of the lights of the line of lights to indicate the condition of the product and positions of the product, and control the visual states of the lights of the line of lights according to the schedule.

15 Claims, 5 Drawing Sheets

LIGHTING APPARATUS FOR CONVEYORS

BACKGROUND

A production facility may use a conveyor system to convey products through a quality control process. The production facility may employ quality control personnel to work along the conveyor to inspect and remove products moving down the conveyor which do not meet quality control specifications. In addition to manual labor, a production facility may rely on automated systems which may detect defective products and sound an alarm when a defective product is detected.

BRIEF DESCRIPTION OF THE DRAWINGS

For a better understanding of the various embodiments described herein and to show more clearly how they may be carried into effect, reference will now be made, by way of example only, to the accompanying drawings in which.

DETAILED DESCRIPTION

A production facility may use a conveyor system to convey products through a quality control process. The production facility may employ quality control personnel to work along the conveyor to inspect and remove products moving down the conveyor which do not meet quality control specifications. In addition to manual labor, a production facility may rely on automated systems which may detect defective products and sound an alarm when a defective product is detected.

It may be challenging, however, to design automated systems which are effective at delivering notifications in the environment of a production facility. The production facility floor may be noisy, which may limit the ability of the personnel to respond to auditory notifications. Further, quality control personnel may have limited time or ability to consult display screens or other devices which may present more rich information.

However, a lighting apparatus may be provided which notifies personnel of the condition of specific products moving along a conveyor. The lighting apparatus may include one or more sensors configured to capture a condition reading of a product and a position reading of the product relative to a path of a conveyor. The lighting apparatus may include a line of lights configured for installation proximate to the conveyor and along the path of the conveyor. The lights of the line of lights may be configurable between different visual states. A controller may be coupled to the one or more sensors and coupled to the line of lights and configured to determine a condition of the product based on the condition reading, determine an initial position of the product relative to a first light of the line of lights based on the position reading, and generate a schedule for controlling visual states of the line of lights. The schedule may control the visual states to indicate the condition of the product and positions of the product as the product is conveyed along the path of the conveyor. The positions of the product may be based on the initial position of the product relative to the first light of the line of lights. The controller may further control the visual states of the lights of the line of lights according to the schedule.

Figure 1:
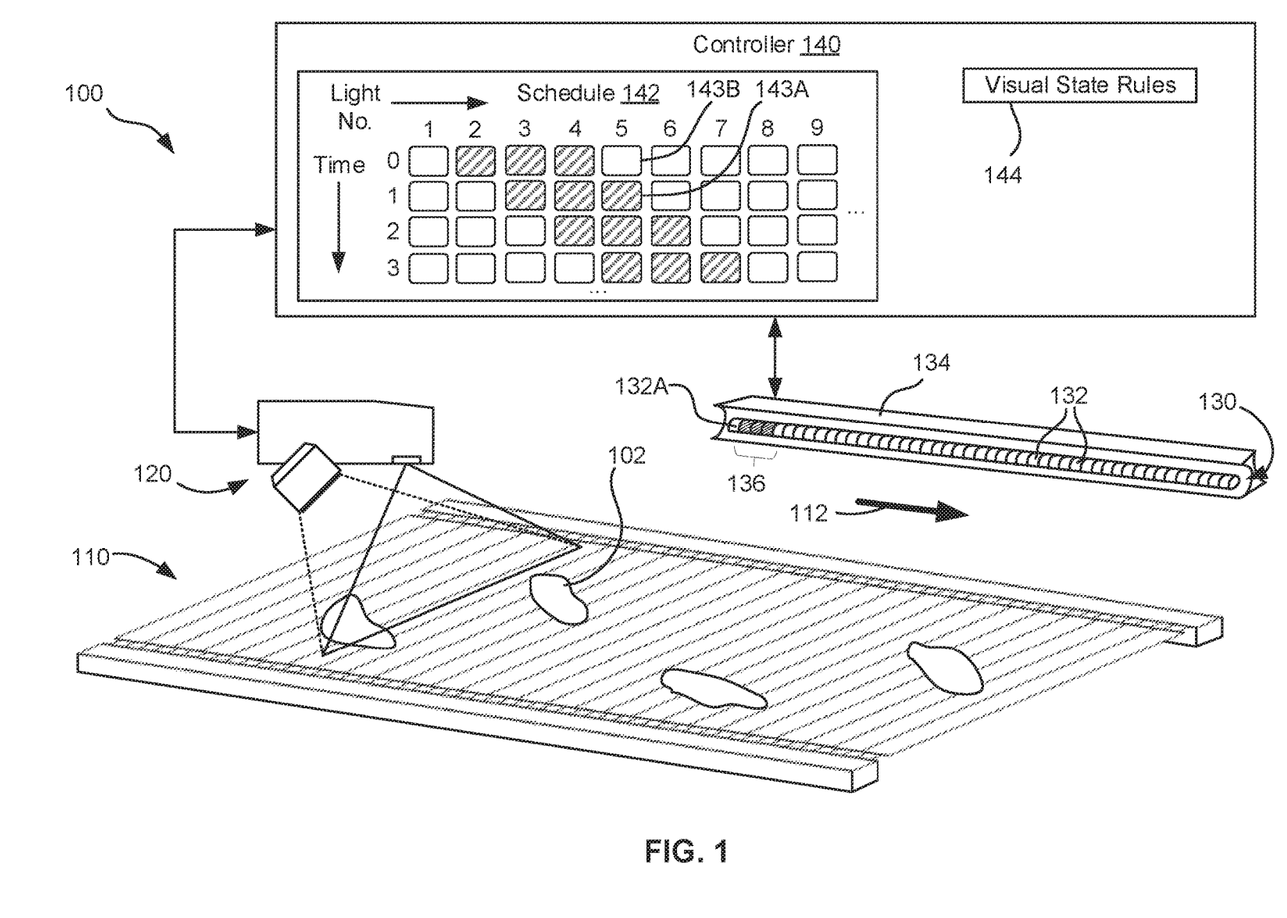
FIG. 1 depicts a schematic perspective view of a lighting apparatus, according to non-limiting examples.

FIG. 1 depicts a schematic perspective view of an apparatus 100 for imaging food products, according to non-limiting examples. The apparatus 100 is configured for installation at a conveyor 110 which moves products 102 along a path 112. The products 102 being conveyed may include food products, such as meats, vegetables, and other food products, which may be inspected for quality or for contamination. The products 102 may also include widgets, apparel, electronics, pharmaceuticals, consumer products, or any goods which could be inspected for quality control purposes.

The apparatus 100 includes an imaging device 120, which is oriented to capture images of products 102 conveyed by the conveyor 110 along the path 112. The imaging device 120 is configured to capture a condition reading of a product 102. In the present example, the imaging device 120 is also configured to capture a position reading of a product 102. The condition reading may include an image of the product 102 from which a condition of the product 102 may be determined through any variety of analytical techniques, including, for example, spectral analysis and image recognition. Thus, an image of a product 102 taken by the imaging device 120 may be used to analyze the product 102 to determine a condition of the product 102. The position reading may also include an image of the product 102 at a known position on the conveyor 110. Thus, an image of a product 102 taken by the imaging device 120 may be used to determine a position of the product 102.

Although in the present example the imaging device 120 captures images of products 102 conveyed by the conveyor 110 along the path 112, it is contemplated that in other examples the imaging device 120 may capture images of products 102 as they are conveyed on another conveyor (not shown) which connects to the conveyor 110, provided that the imaging device 120 takes a position reading of a product 102 relative to the path 112 of the conveyor 110.

The imaging device 120 may include an imager to capture an image, and a lighting device to light the product 102 for imaging. In some examples, the imaging device 120 may include a spectrometer which captures a spectral image, such as a line-scan spectrometer. In yet further examples, the imaging device 120 may comprise a combination of a camera, such as a line-scan camera, and a spectrometer, such as a line-scan spectrometer.

The apparatus 100 further includes a line of lights 130, including individual lights 132, which is configured for installation proximate to the conveyor 110 and along the path 112. The lights 132 of the line of lights 130 are configurable between different visual states, which may be used to indicate the condition and/or position of products 102 moving along the conveyor 110. The lights 132 may include light emitting diode (LED) lights. The LEDs may be monochromatic or multi-colored.

In some examples, as shown, the line of lights 130 may be supported by a support structure 134 to hang the line of lights 130 over the conveyor 110, and generally following the path 112 of the conveyor 110. Thus, the line of lights 130 may be visible to personnel working along a side of the conveyor 110. In other examples, it is contemplated that the line of lights 130 may be supported in other positions by other support structures, provided that the line of lights 130 is positioned proximate to the conveyor 110 and along the path 112 of the conveyor 110. For example, a line of lights 130 may be positioned at a side of the conveyor 110, and either above, or below, the height of a surface of the conveyor 110.

The apparatus 100 further includes a controller 140. The controller 140 is coupled to the imaging device 120 and coupled to the line of lights 130. The controller 140 is configured to determine a condition of a product 102 based on the condition reading. Thus, the controller 140 may determine a condition of a product 102 based on an image of the product 102 captured by the imaging device 120. The controller 140 may determine the condition through any variety of analytical techniques, including, for example, spectral analysis and image recognition. The controller 140, which may store programming instructions, reference spectra, machine learning models, or other data, to make the determinations, may include any combination of a processor onboard the imaging device 120, one or more computing devices in communication with the imaging device 120, and one or more remote computing devices (not shown).

In some examples, the condition to be determined may include a quality of a product 102. For example, where the product 102 includes a food product such as a meat, a quality of the product 102 may include a grade of the meat, fat content of the meat, amount of marbling, or another characteristic related to the quality of a food product. In some examples, a quality of a product 102 may include a presence (or absence) of a contaminant in or on the product 102.

In some examples, the condition to be determined may include a chemical characteristic of a product 102. For example, the condition may include a chemical composition of all ora portion of the product 102, a presence of a chemical on the product 102, a concentration or total amount of a given chemical present in or on the product 102, a relative proportion of two or more chemicals in or on the product 102, or any other chemical characteristic.

In some examples, the condition to be determined may include a physical characteristic of a product 102. For example, the condition may include a color of all ora portion of the product 102, the pH of all ora portion of the product 102, the surface roughness of all ora portion of the product 102, the presence of blemishes or other imperfections to the product 102, a size of the product 102, or another physical characteristic.

The controller 140 is further configured to determine an initial position of a product 102 relative to a first light 132A of the line of lights 130 based on the position reading. For example, the imaging device 120 may capture an image of a product 102 at a location which is a known distance away from the first light 132A, from which a distance from the first light 132A can be determined. For example, the location at which the imaging device 120 captures images may be a known distance ahead of the first light 132A along the path 112.

The controller 140 is further configured to generate a schedule 142 for controlling visual states of the lights 132 of the line of lights 130 to indicate a condition of a product 102 and positions of the product 102 as the product 102 is conveyed along the path 112 of the conveyor 110. The positions of the product 102 as indicated in the schedule 142 are based on the initial position of the product 102 relative to the first light 132A of the line of lights 130. The initial position of a product 102 relative to a first light 132A may be combined with information about the speed of the conveyor 110 and/or the time that would be required for the product 102 to reach the first light 132A to generate the schedule 142. Information about the speed of the conveyor 110 and/or other parameters of the conveyor 110 may be gathered by sensors such as encoders installed on the conveyor 110. In other words, based on the initial position of a product 102 and the time required for the product to reach the first light 132A, the schedule 142 may be generated such that the first light 132A is activated when the product 102 is at a position on the conveyor 110 that is aligned with the first light 132A. Thus, as a product 102 moves along the conveyor 110, the lights 132 of the line of lights 130 may be activated to correspond to a position of the product 102 on the conveyor 110 to indicate positions of the product 102 as the product moves along the conveyor 110.

The controller 140 further controls the visual states of the lights 132 of the line of lights 130 according to the schedule 142. In other words, the controller 140 activates the lights 132 to switch visual states.

As an example of a schedule 142 for controlling visual states of the lights 132, a two-dimensional array is shown having cells indicating the visual states of different lights 132 at different points in time. The "Light No." columns correspond to different lights 132 which are arranged in a line down the line of lights 130, and which are arranged in a line following the path 112. For example, Light No. 1 precedes Light No. 2, and Light No. 2 precedes Light No. 3, and so on, in a direction of path 112. The "Time" rows indicate different points in time, measured in any unit of time.

In the schedule 142, a shaded cell 143A is shaded to indicate that the corresponding light 132 at the corresponding time is in a first visual state. An unshaded cell 143B is unshaded to indicate that the corresponding light 132 at the corresponding time is in a second visual state. The shifting of visual states along the Light Nos. column as time progresses indicates the movement of a product 102 down the path 112.

Various visual state rules 144 are contemplated to dictate how condition and position readings are used to generate a schedule 142. The visual state rules 144 may involve causing lights 132 to adopt different visual states depending on whether a product 102 meets or fails predetermined condition criteria. For example, the visual state rules 144 may dictate that lights 132 which correspond to a location on the conveyor 110 where a product 102 which is of a condition which fails a predetermined condition criteria is present should be in a first visual state, that lights 132 which correspond to a location on the conveyor 110 where no product 102 is present should be in a second visual state, and that lights 132 which correspond to a location on the conveyor 110 where a product 102 which meets a predetermined condition criteria is present should also be in a second visual state. The condition of a product 102 may be determined based on a condition reading of the product 102, such as an image captured by imaging device 120. The predetermined condition criteria may correspond to predetermined quality control specifications set out for the product 102. Various visual indicia is contemplated for the first and second visual states, which may differ in color, intensity, or temporal pattern. More visual states in addition to the first and second visual states (e.g. third and fourth visual states) are also contemplated. Further discussion is provided with reference to FIGS. 4A-4D.

Continuing with reference to FIG. 1, the controller 140 may store the schedule 142 and visual state rules 144 in memory, or may communicate with one or more other computing devices (not shown) to access the schedule 142 and visual state rules 144.

In some examples, the schedule 142 may be generated such that, as a product 102 is conveyed along the path 112 of the conveyor 110, a length 136 of lights 132 of the line of lights 130 are configured to adopt a first visual state, and the other lights 132 of the line of lights 130 may adopt a second visual state different from the first visual state.

In some examples, the length 136 may correspond to a product 102 which is most proximate to a current position of the product 102. In other examples, the length 136 may not necessarily correspond to the most proximate product 102 (e.g. activation of the lights 132 may lead or lag behind movement of the product 102), provided that the lights 132 still provide an indication of a position of products 102 travelling along the path 112.

In some examples, the line of lights 130 is aligned with the path 112 of the conveyor 110. In other examples, the line of lights 130 may be misaligned with the path 112, provided that the lights 132 still provide an indication of a position of products 102 travelling along the path 112. For example, the line of lights 130 may curve around or zig-zag across the path 112.

Figure 2:
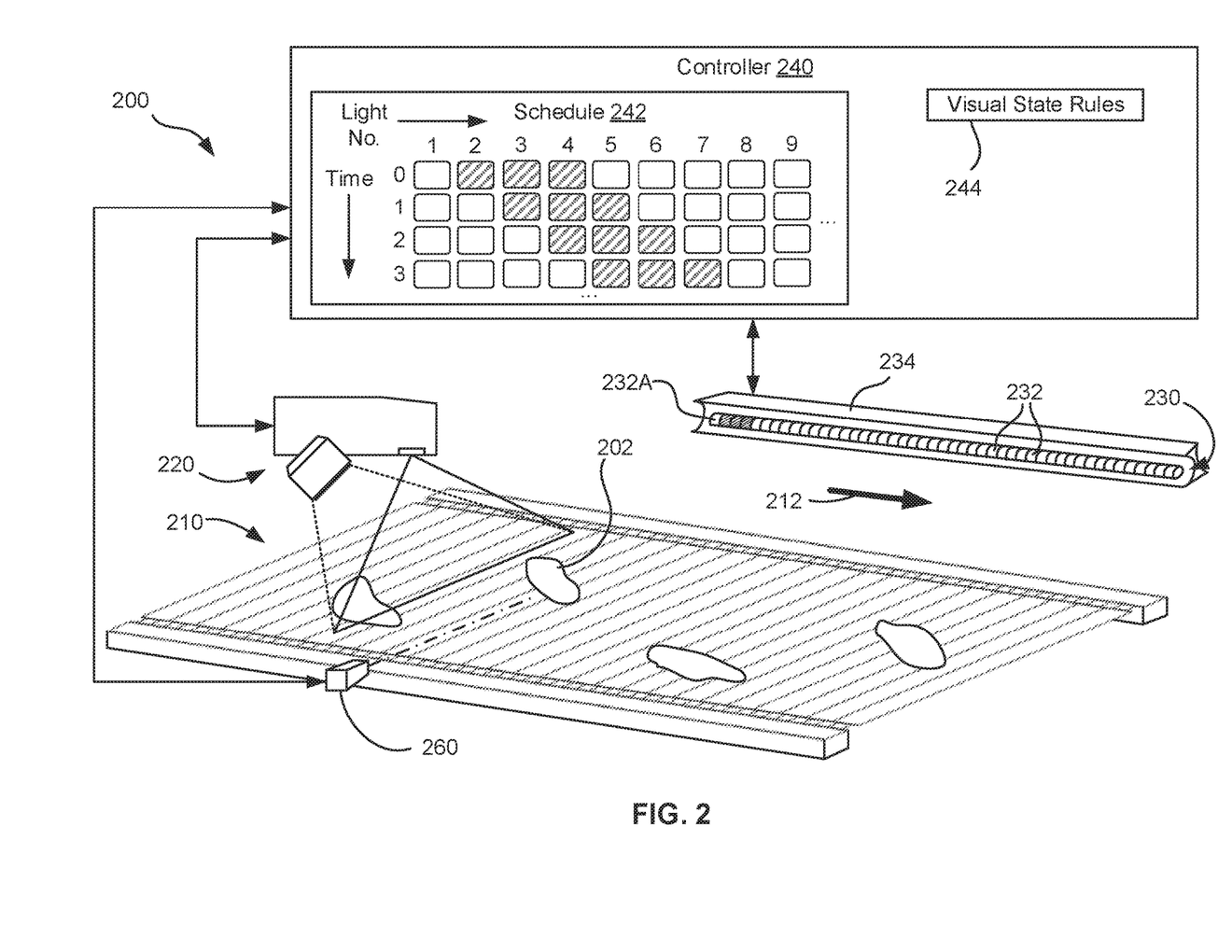
FIG. 2 depicts a schematic perspective view of another lighting apparatus, the apparatus including a proximity sensor, according to non-limiting examples.

FIG. 2 depicts a schematic perspective view of another lighting apparatus 200, according to non-limiting examples. The apparatus 200 is substantially similar to the apparatus 100 with like components having like numbers, however in a "200" series rather than a "100" series.

With reference to FIG. 2, the apparatus 200 hence includes a conveyor 210 to move products 202 in a path 212, an imaging device 220, and a first line of lights 230 having lights 232, supported by support structure 234. The apparatus 200 further includes a controller 240, a schedule 242 and visual state rules 244. For further description of the above elements of the apparatus 200, the description of the apparatus 100 of FIG. 1 may be referenced. For sake of clarity, only the differences between the apparatus 200 and the apparatus 100 will be described in detail.

In contrast to the apparatus 100, the apparatus 200 further includes a proximity sensor 260 to capture position readings of products 202 travelling down the conveyor 210. Thus, the imaging device 220 may not necessarily capture position readings.

The proximity sensor 260 may be configured for installation adjacent the conveyor 210. In some examples, the proximity sensor 260 may be configured for installation adjacent to a side of the conveyor 210 and at or behind a location on the conveyor 210 corresponding to the first light 232A of the line of lights 230. In other examples, the proximity sensor 260 may be configured for installation a distance ahead of, and/or prior to the first light 232A in the path 212. Wherever the proximity sensor 260 captures a position reading of a product 102, that position may be designated to be the initial position of the product 102. As described above with reference to FIG. 1, the initial position of a product 202 may be used to generate the schedule 242 for controlling visual states of the lights 232.

Figure 3:
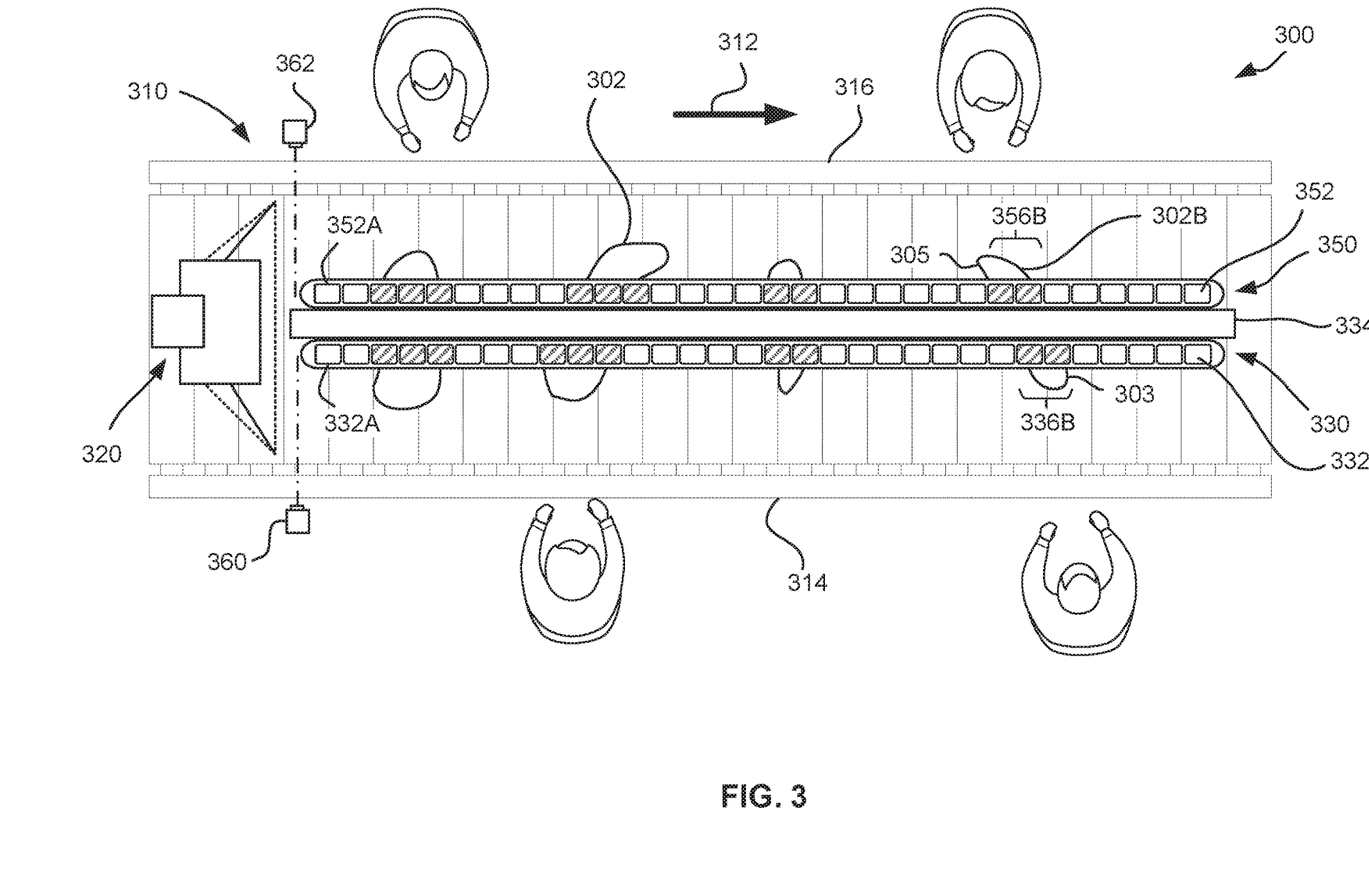
FIG. 3 depicts an overhead plan view of another lighting apparatus, according to non-limiting examples.

FIG. 3 depicts an overhead plan view of another lighting apparatus 300, according to non-limiting examples. The apparatus 300 is substantially similar to the apparatus 100 with like components having like numbers, however in a "300" series rather than a "100" series.

With reference to FIG. 3, the apparatus 300 hence includes a conveyor 310 to move products 302 in a path 312, an imaging device 320, and a first line of lights 330 having lights 332, supported by support structure 334, and a first proximity sensor 360. For further description of the above elements of the apparatus 300, the description of the apparatus 100 of FIG. 1 may be referenced. For sake of clarity, only the differences between the apparatus 300 and the apparatus 100 will be described in detail. Further, a controller has been omitted for clarity, but the apparatus 300 is understood to include a controller similar to the controller 140.

In contrast to the apparatus 100, the apparatus 300 further includes a second line of lights 350 having lights 352. Further, the apparatus 300 includes a second proximity sensor 362.

The second line of lights 350 may be supported by the support structure 334, or by a separate support structure. Further, the conveyor 310 may have a first side 314 and a second side 316. The first line of lights 330 may be configured for installation at the conveyor 310 to be visible predominantly by personnel at the first side 314 of the conveyor 310, and the second line of lights 350 may be configured for installation at the conveyor 310 to be visible predominantly by personnel at the second side 316. For example, the support structure 334 or another component of the apparatus 300 may include shields, barriers, walls, or other hardware which excludes or reduces the visibility of the second line of lights 350 to personnel at the first side 314 of the conveyor 310, and which excludes or reduces the visibility of the first line of lights 330 to personnel at the second side 316 of the conveyor 310. In other examples, the support structure 334 or another component of the apparatus may include optics such as reflectors to enhance visibility of the first line of lights 330 to personnel at the first side 314 of the conveyor 310 and which enhance visibility of the second line of lights 350 to personnel at the second side 316 of the conveyor 310.

Further, the first proximity sensor 360 may be configured for installation adjacent the conveyor 310, and the second proximity sensor 362 may be configured for installation adjacent to the conveyor 310.

In some examples, the first proximity sensor 360 may be configured for installation adjacent to the first side 314 of the conveyor 310 and at or behind a location on the conveyor 310 corresponding to the first light 332A of the first line of lights 330, and/or the second proximity sensor 362 may be configured for installation adjacent to the second side 316 of the conveyor 310 and at or behind a location on the conveyor 310 corresponding to the first light 352A of the second line of lights 350. In other examples, the first proximity sensor 360 may be configured for installation a distance ahead of the first light 332A, and/or the second proximity sensor 362 may be configured for installation a distance ahead of the first light 352A. The proximity sensors 360, 362, need not be aligned. Wherever the proximity sensors 360, 362 capture a position reading of a product 102, that position may be designated to be the initial position of the product 102 for a respective schedule for each line of lights 330, 350.

The first line of lights 330 and the second line of lights 350 may be programmed according to different respective schedules. For example, the schedule for the first line of lights 330 may be generated according to position readings captured by the first proximity sensor 360, and the schedule for the second line of lights 350 may be generated according to position readings captured by the second proximity sensor 362. The differences in the schedules may reflect the orientation of products 302 on the conveyor 310. For example, the proximity sensors 360, 362, may include range sensors or other devices to detect ranges of portions of the products 302 from the proximity sensors 360, 362. The proximity sensors 360, 362 may thereby gather range data which may be used to determine outlines of the products 302 and/or orientations of the products 302. A controller may process the range data to determine an orientation of a product 302, and generate schedules for the lines of lights 330, 350, which reflect the orientation of the product 302.

An example is shown with respect to product 302B, where a leading portion 303 of the product 302B is further down the path 312 and nearer to the first side 314 of the conveyor 310. Further, a lagging portion 305 of the product 302B is behind the leading portion 303 with respect to the path 312 and neared to the second side 316 of the conveyor 310. Thus, the schedule for the first line of lights 330 may include a first length 336B of lights 332, and the schedule for the second line of lights 350 may include a second length 356B of lights 352, with the first length 336B being farther down the path 312.

Having different schedules to control the first line of lights 330 and second line of lights 350 may provide more precise notifications of the positions of products 302 to personnel working on either side of the conveyor 310. However the respective schedules may be generated, the schedules may control the respective lights 332, 352 of the respective lines of lights 330, 350, to correspond to a position of the product 102 on the conveyor 110 to indicate positions of the product 102 as the product moves along the conveyor 110. The respective schedules may differ, as discussed above, to reflect the orientation of products 102 on the conveyor 310.

FIGS. 4A-4D depict example schedules 410, 420, 430, and 440, for controlling visual states of lights of a lighting apparatus, according to non-limiting examples. The schedules 410, 420, 430, and 440 are substantially similar to the schedule 242. For sake of clarity, only the differences from the schedule 242 will be described in detail.

Figure 4A:
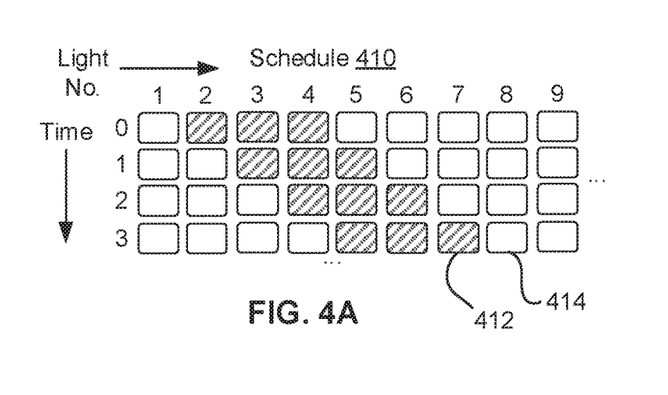
FIGS. 4A-4D depict example schedules for controlling visual states of lights of a lighting apparatus, according to non-limiting examples.

In FIG. 4A, schedule 410 includes shaded cells 412 which are shaded to indicate that the corresponding light at the corresponding time is in a first visual state. Unshaded cells 414 are unshaded to indicate that the corresponding light at the corresponding time is in a second visual state. Lights may adopt a first visual state to indicate the presence of a product which fails to meet predetermined condition criteria. Lights may adopt a second visual state to indicate the presence of a product which meets predetermined condition criteria, or no presence of a product. The first and second visual states may differ in one or more of: color, intensity, and temporal pattern. For example, the first visual state may correspond to a first color, and the second visual state may correspond to the lights being off.

Figure 4B:
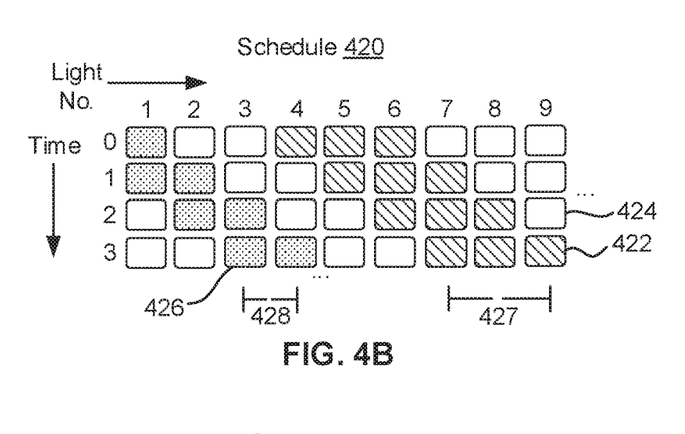

In FIG. 4B, schedule 420 includes shaded cells 422 which are shaded to indicate that the corresponding light at the corresponding time is in a first visual state. Lights may adopt a first visual state to indicate the presence of a first product which fails to meet predetermined condition criteria. The schedule 420 includes unshaded cells 424 which are unshaded to indicate that the corresponding light at the corresponding time is in a second visual state, which may indicate no presence of a product. The schedule 420 includes dotted cells 426 which are dotted to indicate that the corresponding light at the corresponding time is in a third visual state, which may indicate the presence of a second product which fails to meet predetermined condition criteria. Further, the first product may be of a length which corresponds to a length 427 of three lights, and the second product maybe of a length which corresponds to a length 428 of two lights, which indicates that the first product is greater in length than the second product with respect to the path of movement of the products down the conveyor.

Figure 4C:
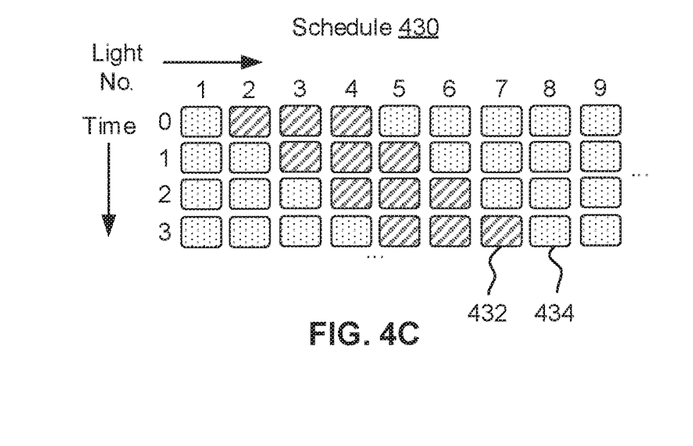

In FIG. 4C, a schedule 430 includes shaded cells 432 which are shaded to indicate that the corresponding light at the corresponding time is in a first visual state. Schedule 430 includes dotted cells 434 which are dotted to indicate that the corresponding light at the corresponding time is in a second visual state. Lights may adopt a first visual state to indicate the presence of a product which fails to meet predetermined condition criteria. Lights may adopt a second visual state to indicate the presence of a product which meets predetermined condition criteria, or no presence of a product. The first and second visual states may differ in one or more of: color, intensity, and temporal pattern. For example, the first visual state may correspond to a first color, and the second visual state may correspond to another color. As another example, the first visual state may correspond to lights in a first temporal state, such as flashing, and the second visual state may correspond to lights in a second temporal state, such as solid color.

Figure 4D:
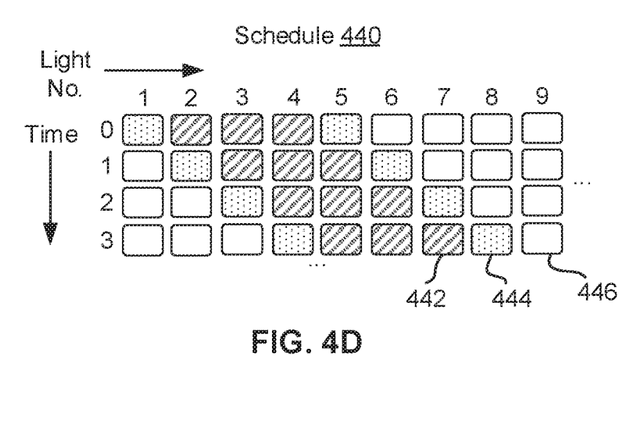

In FIG. 4D, a schedule 440 demonstrates how lights may adopt a visual-spatial pattern to indicate condition and position of products. The schedule 440 includes shaded cells 442 which are shaded to indicate that the corresponding light at the corresponding time is in a first visual state. Lights may adopt a first visual state to indicate the presence and length of a product. Schedule 440 includes dotted cells 444, which outline the shaded cells 442, and which are dotted to indicate that the corresponding light at the corresponding time is in a second visual state. Lights may adopt a second visual state to indicate a condition of the product. Thus, a length of lights may be outlined with lights which indicate a condition of the product. Schedule 440 further includes unshaded cells 446 which are unshaded to indicate that the corresponding light at the corresponding time is in a third visual state. The lights may adopt a third visual state to indicate no presence of a product. The first and second visual states may differ in one or more of: color, intensity, and temporal pattern. For example, the first visual state may correspond to a first color, such as white, to indicate presence of a product; the second visual state may correspond to a second color, such as green, to indicate the product meets a predetermined condition criteria; and the third visual state may correspond to the corresponding lights being switched off, which may indicate no presence of a product.

Thus, it can be seen that lines of lights may be programmed to provide a variety of notifications to quality control personnel regarding the condition of specific products moving along a conveyor. For example, a length of red lights moving along a line of lights may indicate to a quality control personnel that the product beneath the red lights is defective and should be removed from the conveyor. As another example, a length of yellow lights may indicate that a quality control personnel should closely inspect the product because the automated systems were unable to categorize the product as meeting or failing to meet predetermined condition criteria. Further, a green length of lights may indicate that the product beneath the green lights meets predetermined condition criteria. Thus, a quality control personnel may thereby be enabled to work more efficiently, directing attention toward the more important quality control tasks.

Figure 5:
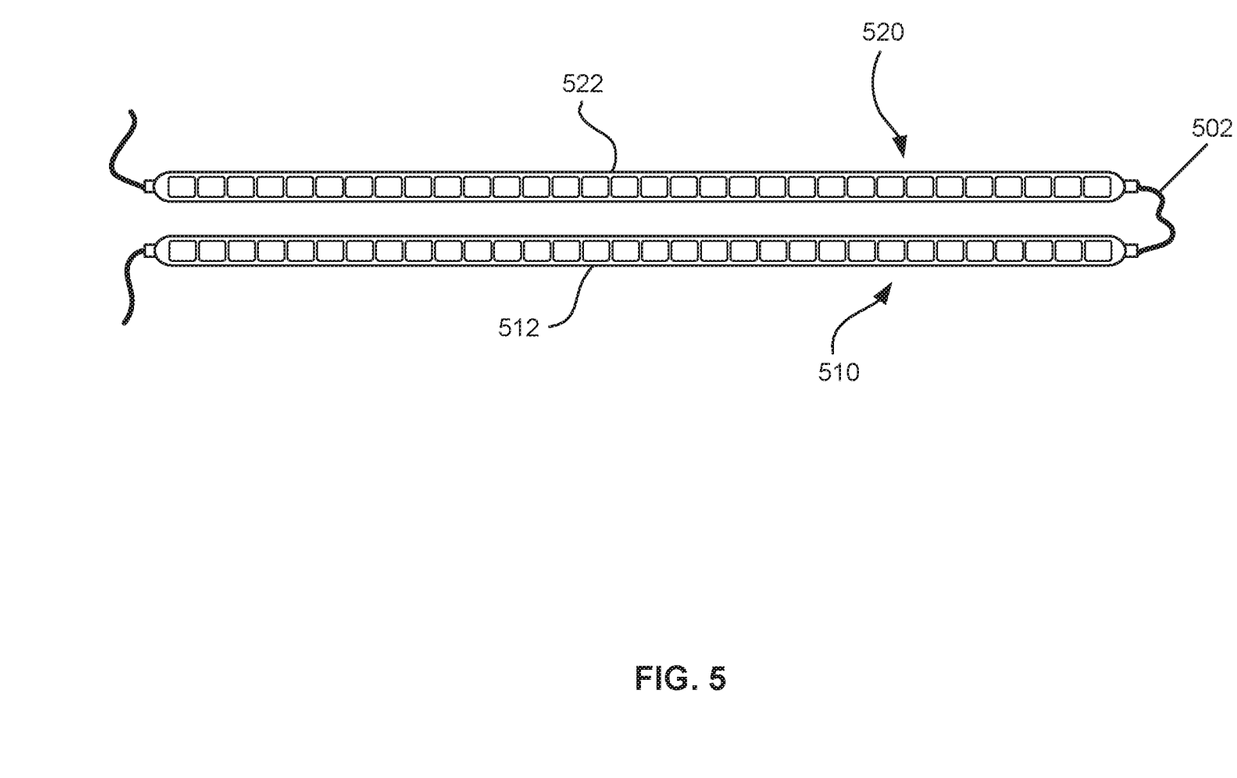
FIG. 5 depicts an overhead plan view of lines of lights, according to non-limiting examples.

FIG. 5 depicts an overhead plan view of lines of lights 510 and 520, according to non-limiting examples. The lines of lights 510 and 520 are substantially similar to the line of lights 130. For sake of clarity, only the differences from the line of lights 130 will be described in detail.

The line of lights 510 may be coupled to the line of lights 520 by a connection 502. The connection 502 may provide power between the lines of lights 510, 520, and may provide communication for a controller to control the lines of lights 510, 520, together, such that individual lines of lights 510, 520, may be joined together into a larger line of lights to span a greater length of conveyor.

The lines of light 510, 520, may be housed in housings 512, 522 configured to transmit light therethrough while protecting components therein. The housings 512, 522 may include food-safe housings suitable for use in a food processing facility.

Thus, it can be seen that a lighting apparatus may be provided which notifies personnel of a condition of a product and a position of the product moving along a conveyor. The lighting apparatus may include a line of lights which are configurable between different visual states, and which may be controlled to indicate a condition of the product and positions of the product as the product moves along the conveyor. Quality control personnel may thereby be notified of the condition of specific products moving down a conveyor to assist the personnel with performing quality control tasks.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XY, YZ, XZ, and the like). Similar logic can be applied for two or more items in any occurrence of "at least one . . . " and "one or more . . . " language.

The terms "about", "substantially", "essentially", "approximately", and the like, are defined as being "close to", for example as understood by persons of skill in the art. In some embodiments, the terms are understood to be "within 10%," in other embodiments, "within 5%", in yet further embodiments, "within 1%", and in yet further embodiments "within 0.5%".

Persons skilled in the art will appreciate that in some embodiments, the functionality of devices and/or methods and/or processes described herein can be implemented using pre-programmed hardware or firmware elements (e.g., application specific integrated circuits (ASICs), electrically erasable programmable read-only memories (EEPROMs), etc.), or other related components. In other embodiments, the functionality of the devices and/or methods and/or processes described herein can be achieved using a computing apparatus that has access to a code memory (not shown) which stores computer-readable program code for operation of the computing apparatus. The computer-readable program code could be stored on a computer readable storage medium which is fixed, tangible and readable directly by these components, (e.g., removable diskette, CD-ROM, ROM, fixed disk, USB drive). Furthermore, it is appreciated that the computer-readable program can be stored as a computer program product comprising a computer usable medium. Further, a persistent storage device can comprise the computer readable program code. It is yet further appreciated that the computer-readable program code and/or computer usable medium can comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium can be either a non-mobile medium (e.g., optical and/or digital and/or analog communications lines) or a mobile medium (e.g., microwave, infrared, free-space optical or other transmission schemes) or a combination thereof.

Persons skilled in the art will appreciate that there are yet more alternative embodiments and modifications possible, and that the above examples are only illustrations of one or more embodiments. The scope, therefore, is only to be limited by the claims appended hereto.

What is claimed is:

1. A lighting apparatus comprising:
   one or more sensors configured to capture a condition reading of a product and a position reading of the product relative to a path of a conveyor;
   a line of lights configured for installation proximate to the conveyor and along the path of the conveyor, the lights of the line of lights configurable between different visual states;
   a controller coupled to the one or more sensors and coupled to the line of lights, the controller configured to:
   determine a condition of the product based on the condition reading;
   determine an initial position of the product relative to a first light of the line of lights based on the position reading;
   generate a schedule for controlling visual states of the lights of the line of lights to indicate the condition of the product and positions of the product as the product is conveyed along the path of the conveyor, the positions of the product based on the initial position of the product relative to the first light of the line of lights; and
   control the visual states of the lights of the line of lights according to the schedule.

2. The lighting apparatus of claim 1, wherein the schedule includes:
   configuring, as the product is conveyed along the path of the conveyor, a length of lights of the line of lights which is most proximate to a current position of the product to adopt a first visual state; and
   configuring other lights of the line of lights to adopt a second visual state different from the first visual state.

3. The lighting apparatus of claim 2, wherein the line of lights is aligned with the path of the conveyor, and wherein the length of lights corresponds to a length of the product.

4. The lighting apparatus of claim 1, wherein the different visual states differ in one or more of: color, intensity, and temporal pattern.

5. The lighting apparatus of claim 1, wherein the one or more sensors comprises a proximity sensor configured for installation adjacent to the conveyor and at or behind a position on the conveyor corresponding to the first light of the line of lights, and wherein the position reading is captured by the proximity sensor.

6. The lighting apparatus of claim 1, wherein the one or more sensors comprises a spectrometer, and wherein the condition reading comprises a spectral image.

7. The lighting apparatus of claim 6, wherein the product comprises a food product.

8. The lighting apparatus of claim 7, wherein the condition of the product comprises a quality of the product.

9. The lighting apparatus of claim 1, wherein the line of lights is housed in a food-safe housing configured to transmit light.

10. The lighting apparatus of claim 1, wherein the condition of the product comprises a chemical characteristic of the product.

11. The lighting apparatus of claim 1, wherein the condition of the product comprises a physical characteristic of the product.

12. A lighting apparatus comprising:
- an imaging device to capture a condition reading of a product;
- a first line of lights configured for installation proximate to the conveyor and along a path of a conveyor, the lights of the first line of lights configurable between different visual states;
- a first proximity sensor configured for installation adjacent to a first side of the conveyor and at or behind a first location on the conveyor corresponding to the first light of the first line of lights, the first proximity sensor to capture a first position reading of the product;
- a second line of lights configured for installation proximate to the conveyor and along the path of the conveyor, the lights of the second line of lights configurable between different visual states;
- a second proximity sensor configured for installation adjacent to a second side of the conveyor and at or behind a second location on the conveyor corresponding to the first light of the second line of lights, the second proximity sensor to capture a second position reading of the product;
- a controller coupled to the imaging device, the first proximity sensor, and the second proximity sensor, the controller configured to:
  - determine a condition of the product based on the condition reading;
  - determine an initial position of the product relative to a first light of the first line of lights and relative to a first light of the second line of lights based on the first position reading and the second position reading;
  - generate a schedule for controlling visual states of the lights of the first line of lights and the second lines of lights to indicate the condition of the product and positions of the product as the product is conveyed along the path of the conveyor, the positions of the product based on the initial position of the product; and
  - control the visual states of the lights of the line of lights according to the schedule.

13. The apparatus of claim 12, wherein the first proximity sensor is configured to detect ranges of portions of the product from the first proximity sensor, the second proximity sensor is configured to detect ranges of portions of the product from the second proximity sensor, and the controller is configured to generate the schedule for controlling visual states of the lights of the first line of lights and the second line of lights to reflect an orientation of the product.

14. The apparatus of claim 12, wherein the apparatus further comprises hardware to reduce visibility of the second line of lights from the first side of the conveyor and to reduce visibility of the first line of lights from the second side of the conveyor.

15. The apparatus of claim 12, wherein the apparatus further comprises optics to enhance visibility of the first line of lights from the second side of the conveyor and to enhance visibility of the second line of lights from the first side of the conveyor.

* * * * *